United States Patent
David et al.

[19]

[11] Patent Number: 6,098,725
[45] Date of Patent: Aug. 8, 2000

[54] SOIL SAMPLING DEVICE WITH FRANGIBLE SECTION AND METHOD OF SAMPLING

[75] Inventors: Ramon R. David, Holland; Saeid Yazdani, Byron Center, both of Mich.

[73] Assignee: SoilCore, Inc., Holland, Mich.

[21] Appl. No.: 09/135,266

[22] Filed: Aug. 17, 1998

[51] Int. Cl.[7] .............................. E21B 49/00; G01N 1/04
[52] U.S. Cl. .............................. 175/58; 175/20; 175/226; 73/864.44; 73/864.45; 73/864.91
[58] Field of Search .............................. 175/20, 58, 226, 175/244, 249, 320; 73/864.44, 864.45, 864.91; 413/12, 15

[56] References Cited

U.S. PATENT DOCUMENTS

| | | |
|---|---|---|
| 1,737,718 | 12/1929 | Hausmann . |
| 1,847,136 | 3/1932 | Rauberstrauch . |
| 2,288,210 | 6/1942 | Schlumberger .............................. 255/1 |
| 2,664,269 | 12/1953 | Knight et al. .............................. 255/1 |
| 3,326,049 | 6/1967 | Eley .............................. 73/429 |
| 3,412,814 | 11/1968 | Rosfelder .............................. 175/6 |
| 3,497,018 | 2/1970 | Shultz et al. .............................. 175/6 |
| 3,970,156 | 7/1976 | Niskin .............................. 175/58 X |
| 4,549,612 | 10/1985 | Cushing .............................. 175/20 |
| 4,729,437 | 3/1988 | Zapico .............................. 175/20 |
| 4,819,735 | 4/1989 | Puckett .............................. 172/22 |
| 4,989,678 | 2/1991 | Thompson .............................. 175/20 |
| 5,245,878 | 9/1993 | Underwood .............................. 73/864.44 |
| 5,343,771 | 9/1994 | Turriff et al. .............................. 73/864.44 |
| 5,505,098 | 4/1996 | Turriff et al. .............................. 73/864.44 |
| 5,517,868 | 5/1996 | Turriff et al. .............................. 73/864.44 |
| 5,522,271 | 6/1996 | Turriff et al. .............................. 73/864.44 |
| 5,706,904 | 1/1998 | Turriff et al. .............................. 175/28 |
| 5,937,953 | 8/1999 | Melberg et al. .............................. 175/20 |

*Primary Examiner*—Eileen Dunn Lillis
*Assistant Examiner*—Jong-Suk Lee
*Attorney, Agent, or Firm*—Van Dyke, Gardner, Linn & Burkhart, LLP

[57] ABSTRACT

A soil sampling device for collecting samples of soil provides a single use unit with an integrally molded plunger. The soil sampling includes a cylindrical body having first and second ends, with the body comprising a cylindrical wall having a longitudinal axis and an end wall. The cylindrical wall extends between the first and second ends of the body, with the end wall being positioned at the first end of the body. The second end of the body defines a mouth which is adapted for inserting into soil. A piston is positioned in the body, and the end wall includes a projecting member extending outwardly from the body which defines a plunger. The end wall includes reduced cross-section around the projecting member and is adapted to break when a force is applied to the projecting member to thereby permit the plunger enter into the body and thereby push the piston along the longitudinal axis to expel a sample of soil collected in the body. Preferably, the piston is frictionally held in the body, for example by frictionally engaging an inner surface of the cylindrical wall. Optionally, the piston includes at least one seal for frictionally engaging the inner surface of the cylindrical wall.

50 Claims, 3 Drawing Sheets

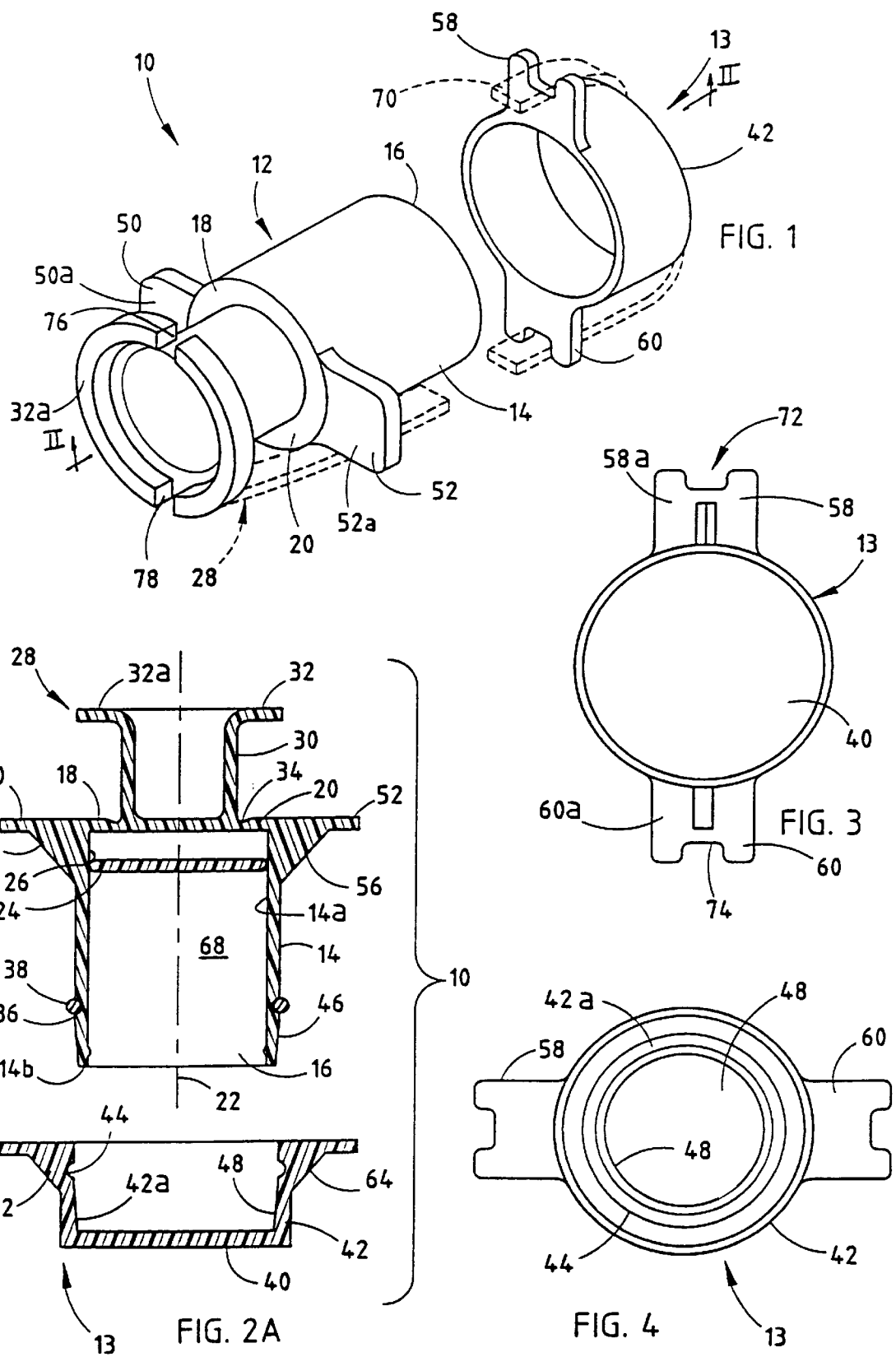

SOIL SAMPLING DEVICE WITH FRANGIBLE SECTION AND METHOD OF SAMPLING

TECHNICAL FIELD AND BACKGROUND OF THE INVENTION

The present invention relates to a soil sampling device and, more particularly, to a elf contained soil sampling device for obtaining soil samples for soil testing.

Soil sampling devices are used to obtain a sample of soil for analyzing the soil content including, for example, volatile organic compounds (VOCs) which may have permeated the soil. Typically, soil sampling devices include a barrel which includes an open end for inserting into the soil and a plunger which is adapted to extend through the barrel to expel the collected soil sample from the barrel for subsequent testing. Often, the soil sampling devices include a removable cover which is placed over the open end of the barrel after the soil sample has been taken so that the soil sampling device can be transported to a laboratory setting, including for example testing facilities which may be located at the soil sampling site, where the cap is then removed and the soil is expelled from the barrel by the plunger.

For example, in U.S. Pat. No. 5,706,904 to Turriff et al., a reusable soil sampling device is disclosed which includes a barrel and a plunger assembly. The plunger assembly includes a shaft which extends to the end wall of the barrel and a piston mounted to the distal end of the shaft and a pair of outwardly extending arms mounted to the medial portion of the shaft. Initially, the plunger assembly is fully extended into the barrel such that the plunger is generally positioned at the mouth of the barrel. When taking a soil sample, however, the plunger is pulled through the barrel, somewhat like a syringe, during which time the barrel is filled with soil. The Turriff piston includes a pair of seals which engage the inner surface of the barrel to minimize the loss of the VOCs in the soil during the filling of the barrel. Once the barrel is completely filled with the soil sample, the arms of the piston assembly are rotated and seated in a holding structure provided on the end wall of the barrel. In this manner, the piston assembly is in a fixed, fully retracted position in the barrel. In order to expel the soil sample from the barrel, the arms are then rotated back to a release position so that the plunger can then be again extended into the barrel to thereby expel the soil sample from the barrel with the piston. However, it has been found that the piston assembly is hard to manipulate, and that over time, the space between the shaft of the piston and the end wall of the barrel may become clogged with soil and, thus, prevent the piston from properly operating.

In U.S. Pat. No. 5,343,771, another reusable soil sampling device is disclosed which includes a barrel and a piston assembly which is slidably mounted in the barrel through an end wall of the barrel. The piston assembly includes a shaft and a piston on one end of the shaft and a handle on the opposed end of the shaft. The piston assembly is biased in a retracted position in the barrel by a spring which is positioned between the handle and a handle of the barrel. The soil sampling device further includes a cap which is mounted to the open end of the barrel after the soil sample has been taken. Other such arrangements can be found in U.S. Pat. No. 3,326,049 to Eley. In the Eley device, the plunger assembly includes a scale on the shaft of the plunger assembly in order to read the displaced volume of the sample when soil is expelled from the barrel. The Eley sampling device permits several samples to be taken from a single core sample.

In U.S. Pat. No. 5,522,271 to Turriff et al., a soil sampling device is disclosed which includes a barrel and a plug, which is integrally molded with the barrel. The plug is positioned inside the barrel and is spaced from the mouth portion. The plug includes a frangible section which is integrally molded with the barrel. In order to obtain a soil sample, however, the frangible section must be supported by a support member which is inserted into the second open end of the barrel and extended into the barrel to make direct contact with the plug. After a soil sample has been taken, a cap is placed over the open end of the barrel to retain the soil sample therein. In order to expel the soil sample for later testing, the support member is removed from the barrel and a second device (55) is inserted into the barrel to apply a force to the plug to thereby break the frangible section in order to expel the soil sample. Thus, the Turriff '271 soil sampling device requires four components: The barrel; the cap; the support member; and the expulsion device (55). As a result, the Turriff '271 device is relatively complicated to use and ultimately, as a result of the several component parts, is more costly than most conventional sampling devices.

Consequently, there is a need for a simple single use soil sampling device which maintains the integrity of the VOCs in the soil sample, and yet provides the ease of sampling and expulsion of the collected soil sample with fewer steps and fewer components than heretofore known.

SUMMARY OF THE INVENTION

Accordingly, the present invention provides a new and unique soil sampling device, which is especially suitable for collecting samples of soil for measuring the VOCs in the soil sample. The soil sampling device includes an improved piston assembly which is easy to use and requires fewer component parts.

According to one aspect of the invention, a soil sampling device includes a body and a piston positioned in the body. The body comprises a cylindrical wall having a longitudinal axis and an end wall, with the cylindrical wall extending between first and second ends of the body. The end wall is positioned at the first end of the body, and the second end of the body defines a mouth, which is adapted for inserting into the soil. The end wall includes a projecting member which extends outwardly from the body and which defines a plunger. The end wall includes a reduced cross section around the projecting member and is adapted to break when a force is apply to the projecting member to permit the plunger to enter into the body and, thereby, push the piston along the longitudinal axis of the body to expel a sample of soil collected in the body.

In preferred aspects of the invention, the piston is frictionally held in the body. For example, the piston may frictionally engage in an inner surface of the cylindrical wall. In a further aspect, the piston may include at least one seal, for frictionally engaging the inner surface of the cylindrical wall of the soil sampling body.

In other aspects, a soil sampling device further includes a cap, which closes the second end of the body after a soil sample has been taken. The cap is preferably releasably mounted to the body at the second end. For example, the cap may be frictionally held on the body. In one form, the cap includes a tapered inner surface, which frictionally engages an end portion of the cylindrical wall to thereby frictionally hold the cap on the body of the second end.

In other forms, the body includes a seal, which seal frictionally holds the cap on the body. For example, the seal may comprise a strip seal or an O-ring seal. In preferred form, either the body or the cap includes a groove for holding the seal on the soil sampling device. In further forms, a second groove may be provided on the other of the body or the cap to receive the seal.

In yet other aspects, the reduced cross-section of the end wall is positioned radially inward of the cylindrical wall of the body. Furthermore, the reduced cross-section of the end wall preferably comprises an annular groove on the outer surface of the end wall which extends around the projecting member.

In other aspects of the invention, a method of sampling a soil includes providing a soil sampling device. The soil sampling device includes a body with first and second ends. The body of the soil sampling device includes a cylindrical wall and an end wall, with the cylindrical wall extending between the first and second ends of the body, and the end wall being positioned at the first end of the body. The second end of the body defines a mouth which is adapted for inserting into soil. The soil sampling device further includes a piston which is positioned in the body and a projecting member which extends outwardly from the end wall of the body. The projecting member defines a plunger. The end wall of the body includes an annular frangible section at an innerface between the plunger and the end wall. The mouth of the soil sampling device is inserted into the soil and subsequently removed to thereby collect a sample of soil. In order to eject the soil sample from the body of the soil sampling device, a force is applied to the projecting member to thereby break the frangible section of the end wall. The projecting member is then pushed into the body of the soil sampling device after breaking the frangible section to thereby expel the piston and the sample of the soil collected from the body of the soil sampling device.

In further aspects, the piston is retained in the body of the soil sampling device after the soil sample has been expelled from the body. In addition, the mouth of the body of the soil sampling device preferably is covered after removing the soil sampling device from the soil to retain integrity of the collected sample of soil.

As will be understood, the soil sampling device of the present invention provides numerous advantages over prior known soil sampling devices. The soil sampling device provides a single use device which consists of two parts, the soil sampling device body and piston and the cap. The soil sampling device is simple to use and overcomes the handling problems of prior known soil sampling devices since the plunger assembly is integrally molded with the end wall of the soil sampling device body and is not actuated until impacted. Furthermore, the piston which ejects the soil sample from the body of the soil sampling device, is preferably retained in the soil sampling device to minimize contamination of the soil sample. Furthermore, the previous requirements of manual dexterity are completely eliminated, thereby reducing the sampling time. These and other objects, advantages, purposes, and features of the invention will become more apparent from the study of the following description taken in conjunction with the drawings.

BRIEF DESCRIPTION OF THE DRAWINGS

FIG. 1 is an exploded perspective view of a soil sampling device of the present invention;

FIG. 2A is a cross-sectional view of the soil sampling device of FIG. 1 taken along line II—II;

FIG. 3 is an outside plan view of the cap of the soil sampling device of FIG. 1;

FIG. 4 is an inside plan view of the cap of FIG. 3;

DESCRIPTION OF THE PREFERRED EMBODIMENTS

Figure 2B:
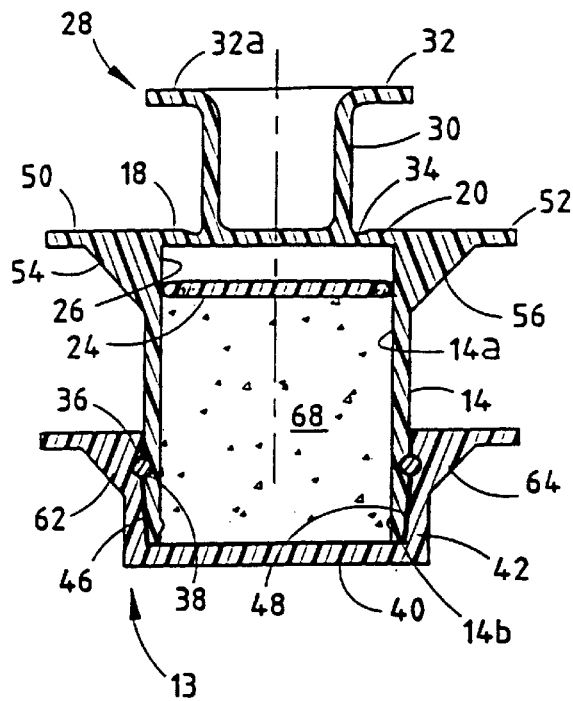
FIG. 2B is a similar view to FIG. 2A with the cap mounted to the body of the soil sampling device.

Referring to FIG. 1, the numeral 10 generally designates a soil sampling device of the present invention. Soil sampling device 10 includes a cylindrical body 12 and a cap 13. Body 12 preferably comprises a plastic material, such as a polymer. More preferably, body 12 comprises a reinforced polymer, such as a glass reinforced polyphthalamide (PPA) and, most preferably, a AMODEL® A-1145 HSPPA Resin, which is available from Amaco Polymers Inc. of Alpharetta, Ga. As will be more fully described below, soil sampling device 10 is formed or arranged so that when a soil sample is taken, gasses and other particles which may be present in the soil will remain generally undisturbed during the soil sampling process so that an accurate analysis may be performed in a laboratory located either on or off the soil sampling site location.

Cylindrical body 12 includes a cylindrical wall 14 which defines an open end 16 of body 12 on one end and which is closed on the other end 18 by an end wall 20. Open end 16 defines a mouth of sampling device 10 for inserting into soil so that a soil sample can be collected in body 12 of soil sampling device 10. Cylindrical wall 14 extends between end wall 20 and open end 16 along a longitudinal axis 22 of body 12 (FIG. 2A).

Referring to FIG. 2A, a piston 24 is positioned in cylindrical body 12. Piston 24 is held in a chamber 68 defined in body 12 by friction. As best seen in FIG. 2A, piston 24 comprises a dish-shape body having an outer peripheral portion 26 which frictionally engages inner surface 14a of cylindrical wall 14. As will be more fully described below, piston 24 may include one or more seals for frictionally engaging inner surface 14a of cylindrical wall 14. Piston 24 is preferably positioned toward end wall 20 and spaced from open end 16 of cylindrical wall 14. However, it should be understood, that piston 24 may positioned adjacent open end 16 of cylindrical wall 14 before insertion of the soil sampling device into the soil whereby the piston 24 moves along longitudinal axis 22 towards closed end 20 during the collection of a soil sample.

Extending from end wall 20 of body 12 is a projecting member 28. In the illustrated embodiment, projecting member 28 comprises a flanged cylindrical body having a cylindrical wall 30 which is spaced inwardly of cylindrical wall 14 of cylindrical body 12 and which includes an outwardly extending flange 32 to define a contact surface 32a, as will be more fully described below. It should be understood, however, that projecting member 28 may comprise a solid flanged cylindrical body. Preferably, projecting member 28 is integrally molded with end wall 20 to form a unitary soil sampling device. As best seen in FIG. 2A, end wall 20 includes an annular groove 34, which extends around projecting member 28. Annular groove 34 forms a reduced cross-section for end wall 20 and further provides for increased stress concentration factors at the juncture or interface between projecting member 28 and end wall 20. By reducing the cross-section of end wall 20 and increasing the stress concentration factors, annular groove 34 forms a frangible section, which will be more fully explained below.

Again referring to FIG. 2A, cylindrical wall 14 of body 12 includes an annular groove 36 adjacent open end 16 in which a seal 38 is positioned for frictionally engaging cap 13 on open end 16. Cap 13 includes a base or end wall 40 and an annular wall 42 which projects —from base 40 for extending over the end portion of cylindrical wall 14 at open end 16. Optionally, inner surface 42a of annular wall 42 of cap 13 includes an annular groove 44 which corresponds and is generally aligned with annular groove 38 of cylindrical wall 14 when cap 13 is placed on cylindrical wall 14. In this manner, when cap 13 is mounted to open end 16 of cylindrical body 12, seal 38 will seat in annular groove 44 and frictionally hold cap 13 on cylindrical wall 14.

Figure 5:
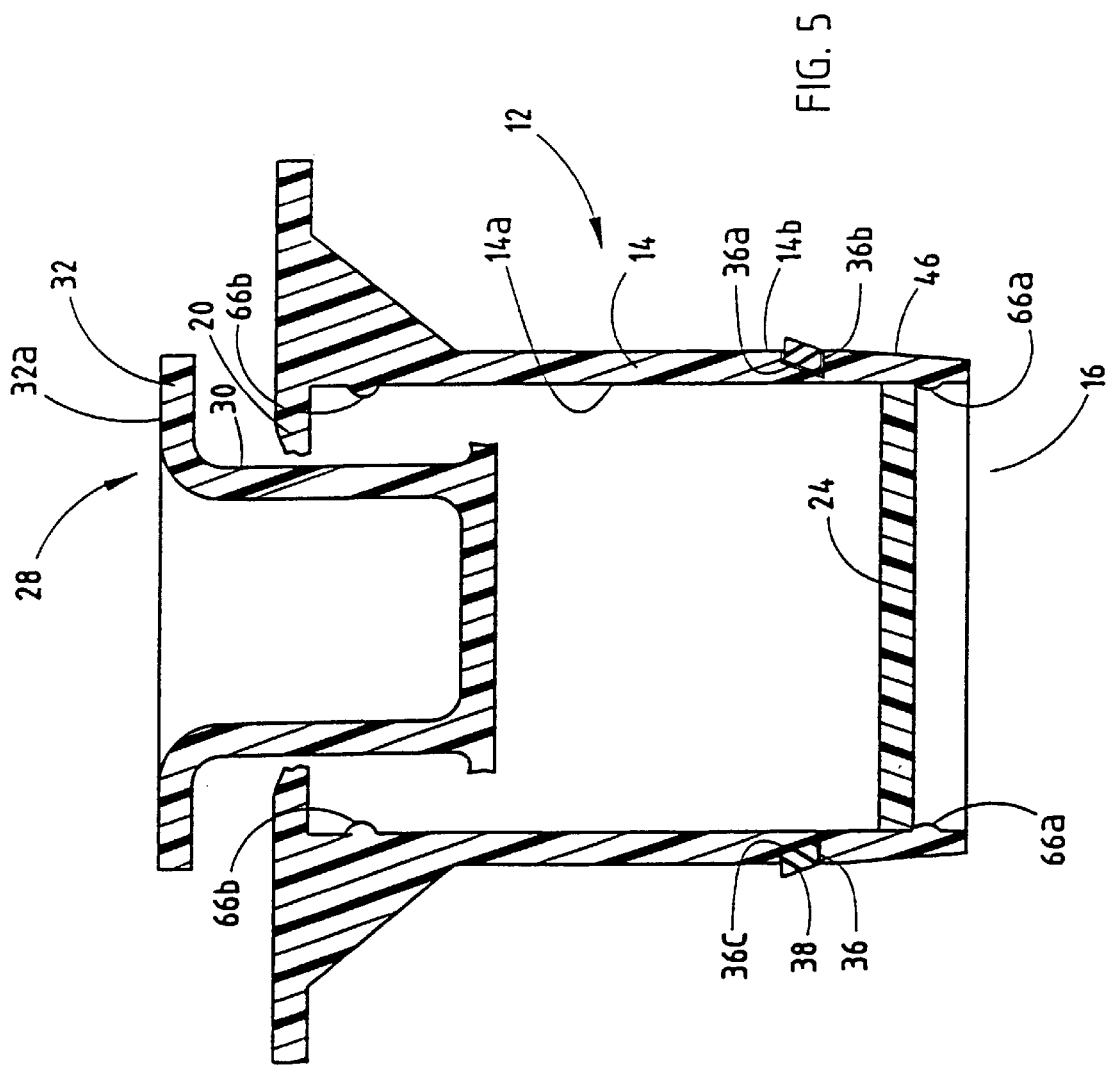
FIG. 5 is an enlarged cross-sectional view similar to FIG. 1.

Referring to FIGS. 2A and 5, cylindrical wall 14 of body 12 preferably further includes a tapered end portion 46 to ease insertion of body 12 into soil. Furthermore, cap 13 optionally includes a tapered surface 48 on inner surface 42a of annular wall 42 which guides tapered surface 46 of cylindrical wall 14 inwardly when cap 13 is placed on to cylindrical wall 14 at open end 16. In this manner, tapered surface 48 provides further frictional engagement of cap 13 with cylindrical wall 14 of body 12. In addition, referring to FIG. 2B, distal end 14B of cylindrical wall 14 of body 12 contacts or bears against base 40 to thereby eliminate head space between the soil in body 12 and base 40 of cap 13.

To further ease insertion of body 12 into soil, body 12 optionally includes a pair of outwardly extending flanges 50 and 52 which respectively define pressing surfaces 50a and 52a. As best seen in FIG. 2, projecting arms 50 and 52 are integrally molded with body 12 and are positioned near or at closed end 18 of body 12 and are generally flush with end wall 20 of body 12. Optionally, each projecting arm 50, 52 is reinforced by a respective gusset 54 and 56, which likewise may be integrally molded with body 12. In a similar manner, cap 13 may include outwardly projecting arms 58 and 60 which respectively define pressing surfaces 58a and 60a to ease mounting or securement of cap 13 onto body 12 and ease the subsequent removal of cap 13 from body 12. Furthermore, arms 58 and 60 may be reinforced by gusset 62 and 64.

Referring again to FIG. 5, in preferred form, seal 38 comprises a strip seal with a generally rectangular cross-section. Additionally, groove 36 preferably comprises a trapezoidal or similar shaped groove which includes a base wall portion 36a which is angled with respect to the outer surface 14b of cylindrical wall 14. In this manner, when seal 38 is positioned in groove 36, seal 38 is substantially recessed within groove 36 at the bounding side wall 36b of groove 36, which is closer to open end 16, and projects outwardly from groove 36 at bounding side wall 36c of groove 36, which is spaced further from open end 16, for engagement with end cap 13. In this manner, when body 12 is inserted into soil, seal 38 will be compressed against bounding side wall 36c and will remain essentially in place in groove 36, which is particularly suitable for clay soil sampling. In clay soil sampling, the soil tends to pull or twist seals which project outwardly over the full width of the groove. Furthermore, inner surface 14a of cylindrical wall 14 preferably includes one or more retaining ribs 66a which retain piston 24 in body 12. Optionally, projecting rib 66a may comprise an annular projecting ring which extends around the full perimeter of inner surface 14a of cylindrical wall 14. In this manner, piston 24 is retained and not ejected along with the soil sample when the soil sample is expelled from body 12. In addition, inner surface 14a optionally includes a second retaining rib 66b adjacent end wall 20 for limiting the upper movement of piston 24. Therefore, piston 24 is movable between upper and lower positions in body 12 as defined by ribs 66a and 66b. In this manner, the upper most position of piston 24 may define a fixed volume.

Referring again to FIGS. 1, 3 and 4, soil sampling device 10 may further include a holding device 70, for example a strap or a tie. Holding device 70 provides for additional securement of cap 13 to body 12 after a soil sample has been collected. As best seen in FIG. 1, holding device 70 extends over cap and over projecting member 28 to thereby anchor cap 13 to body 12. In order to prevent holding device 70 from shifting, cap 13 may optionally include channel-shaped grooves or recesses 72 and 74 in projecting arms 58 and 60. Recesses 72 and 74 define guides for holding device 70. Furthermore, projecting flange 32 of projecting member 28 may similarly include slotted openings 76 and 78 to likewise receive holding device 70 to further assure that holding device 70 will remain on body 12 and cap 13. It should be understood, that holding device 70 may comprise a conventional tie-wrap or a strap with a corresponding buckle. In this manner, cap 13 will remain on body 12 until soil sampling device 10 reaches the laboratory.

From the foregoing, it can be appreciated that an improved method of taking a soil sample is disclosed. First, open end 16 of body 12 is inserted into soil by applying a compressive force to pressing surfaces 50a and 52a. After chamber 68 is filled with soil, body 12 is removed from the soil by pulling on projecting arms 50 and 52. Once removed from the soil, cap 13 is pressed onto cylindrical wall 14 at open end 16 of body 12 to thereby seal the soil sample in chamber 68. Optionally, holding device 70 may be wrapped around cap 13 and body 12 to thereby further secure cap 13 onto body 12. Once transported to a laboratory, holding device 70 is removed and cap 13 is pulled off open end 16 of body 12. Preferably, body 12 is oriented in a generally vertical orientation and a force, such as impact force, is applied to contact surface 32a of projecting member 28 with a sufficient magnitude to break the frangible section defined by annular recessed groove 34. Once the frangible section is broken, projecting member 28 is pressed into body 12 to contact piston 24 and push piston 24 to thereby expel the soil sample from chamber 68 of body 12. Preferably, projecting rib 66a retains piston 24 in body 12 to thereby eliminate contamination of the soil. After the soil sample is expelled, the soil sampling device 10 is discarded and can not be reused.

Figure 6:
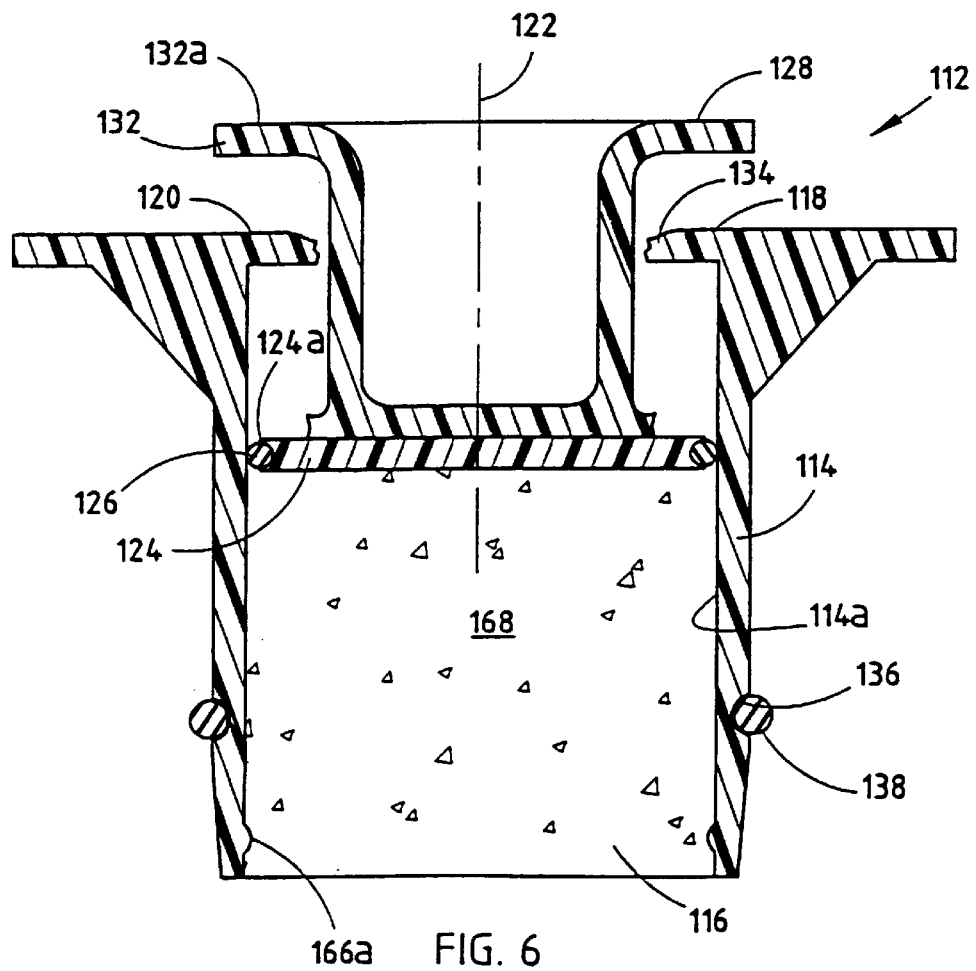
FIG. 6 is a cross-sectional view similar to FIG. 5 illustrating a second embodiment of the soil sampling device of the present invention.

Referring to FIG. 6, a second embodiment of cylindrical body 12 is illustrated. Similar to body 12, cylindrical body 112 includes a cylindrical wall 114 which extends between an open end 116 and a closed end 118. Closed end 118 is defined by an end wall 120. Extending from closed end 120 is a projecting member 128 which is integrally formed with end wall 120. Projecting member 128 has a similar construction to projecting member 28 is integrally molded with end wall 120. End wall 120 includes an annular ring 134 which extends around projecting member 128. Optionally, annular ring 134 comprises a material which has a reduced strength and, therefore, forms a frangible section in end wall 120. Such dissimilar inserts may be achieved by, for example, co-injection molding which is well known in the molding art.

Positioned inside body 112 is a piston 124 which optionally includes at least one seal 126 at its outer peripheral portion 124a for frictionally engaging inner surface 114a of cylindrical wall 114. In the illustrated embodiment, seal 126 comprises an O-ring seal; however, it should be understood that piston 124 may include other suitable seals for frictionally engaging inner surface 114a. Again in a similar manner to the previous embodiment, inner surface 114a of cylindrical wall 114 includes one or more projecting ribs 166 which retain piston 124 in body 112 when the soil sample is ejected from body 112.

As best seen in FIG. 6, end wall 120 optionally has a thinner wall thickness than cylindrical wall 114 to thereby ensure that when a force is applied to projecting member that the end wall 120 will break at recessed groove 134.

In order to retain the cap (which is not shown in this embodiment), cylindrical wall 114 includes a semi-circular groove 136 in which an O-ring seal 138 is positioned for frictionally engaging the cap. Sampling device 110 is more suitable for sampling soils with greater sand content, which unlike clay soil will not tend dislodge seal 138 from groove 136. It should be understood from the foregoing, that body 112 is inserted into the soil in a similar fashion to body 12 of the first embodiment of the soil sampling device. Furthermore, a force is applied to contact surface 132a of projecting member 128 to break frangible section 134 so that projecting member 128 may extend into body 112 and push piston 124 along the longitudinal axis 122 of body 112 to thereby expel the soil contained in chamber 168 of body 112.

While several forms of the invention have been shown and described, other forms will now become apparent to those skilled in the art. For instance, body 12 or 112 may be formed from a metal material with the frangible section being formed by an insert which is interposed between the projecting member and the end wall of the body of the soil sampling device. Furthermore, end wall 20 or 120 may have an overall reduced wall thickness such that end wall 20 or 120 is thinner than cylindrical wall 14 or 114, as described previously, but with out notch or groove 34 or 134. Thus, end wall 20 or 120 comprises the frangible section. In addition, end wall 20 or 120 may have a variable wall thickness to further control the failure mode of end wall 120 or the frangible sections. The embodiment of the invention shown in the drawings is not intended to limit the scope of the invention which is defined by the claims which follow.

We claim:

1. A soil sampling device comprising:
  a body having first and second ends, said body comprising:
    a cylindrical wall having a longitudinal axis and an end wall, said cylindrical wall extending between said first and second ends of said body, said end wall positioned at said first end of said body, said second end of said body defining a mouth, and said mouth being adapted for inserting into soil;
  a piston positioned in said body, and
  said end wall including a projecting member extending outwardly from said body, and said end wall being adapted to break when a force is applied to said projecting member to permit at least a portion of said projecting member to enter into said body and push said piston along said longitudinal axis to thereby expel a sample of soil collected in said body.

2. The soil sampling device according to claim 1, wherein said second end of said body includes a tapered portion to ease insertion of said body into the soil.

3. The soil sampling device according to claim 1, wherein said projecting member is integrally formed with said end wall.

4. The soil sampling device according to claim 1, wherein said piston comprises a disc-shaped member.

5. The soil sampling device according to claim 1, wherein said piston is frictionally held in said body.

6. The soil sampling device according to claim 5, wherein said piston frictionally engages an inner surface of said cylindrical wall.

7. The soil sampling device according to claim 5, wherein said piston includes at least one seal, said seal frictionally engaging said inner surface of said cylindrical wall.

8. The soil sampling device according to claim 1, further comprising a cap, said cap closing said second end of said body.

9. The soil sampling device according to claim 8, wherein said cap is releasably mounted to said body at said second end.

10. The soil sampling device according to claim 9, wherein said cap is frictionally held on said body.

11. The soil sampling device according to claim 10, wherein said cap includes a tapered inner surface, said tapered inner surface frictionally engaging an end portion of said cylindrical wall to thereby frictionally hold said cap on said body at said second end.

12. The soil sampling device according to claim 8, wherein said cap includes a base wall, said cylindrical wall having a distal end abutting said base wall when said cap closes said second end of said body.

13. The soil sampling device according to claim 11, wherein one of said body and said cap includes a seal, said seal frictionally holding said cap on said body.

14. The soil sampling device according to claim 13, wherein said seal is selected form the group consisting of an o-ring seal and a strip seal.

15. The soil sampling device according to claim 13, wherein said one of said body and said cap includes a groove for holding said seal.

16. The soil sampling device according to claim 15, wherein another of said body and said cap includes a groove for receiving said seal.

17. The soil sampling device according to claim 1, wherein at least a portion of said end wall includes a reduced cross-section, said reduced cross-section being adapted to break when a force is applied to said projecting member.

18. The soil sampling device according to claim 17, wherein said end wall and said cylindrical wall each have a wall thickness, said wall thickness of said end wall and said wall thickness of said cylindrical wall being generally equal, and said reduced cross-section of said end wall having a thickness less than said wall thicknesses of said end wall and said cylindrical wall.

19. The soil sampling device according to claim 17, wherein said reduced cross-section of said end wall is positioned radially inward of said cylindrical wall of said body.

20. The soil sampling device according to claim 19, wherein said reduced cross-section of said end wall comprises an annular groove in an outer surface of the end wall, said annular groove extending around said projecting member.

21. The soil sampling device according to claim 1, wherein said end wall and said cylindrical wall each have a wall thickness, said wall thickness of said end wall being less than said wall thickness of said cylindrical wall.

22. The soil sampling device according to claim 1, wherein said body includes at least one projecting arm, said projecting arm extending radially outward from said body to thereby provide a pressing surface to ease insertion of said body into the soil.

23. The soil sampling device according to claim 22, wherein said projecting arm is positioned at said first end of said body.

24. The soil sampling device according to claim 22, wherein said projecting arm is generally flush with an upper surface of said end wall.

25. The soil sampling device according to claim 22, wherein said projecting member is reinforced by a gusset.

26. The soil sampling device according to claim 22, wherein said projecting arm comprises a pair of radially outwardly extending flanges, said flanges defining a pair of pressing surfaces.

27. The soil sampling device according to claim 1, wherein said projecting member includes a radially outwardly extending flange, said flange including a recess, said recess being adapted for receiving a holding device for securing said cap to said body.

28. The soil sampling device according to claim 1, further comprising a holding device, said holding device securing said cap to said body thereby providing additional securement of said cap to said body.

29. The soil sampling device according to claim 28, wherein said holding device comprises a strap, said strap extending over said cap and said body.

30. The soil sampling device according to claim 1, wherein said projecting member of said end wall includes a projecting flange, said projecting flange defining a contact surface on which the force is applied to break said end wall.

31. The soil sampling device according to claim 1, wherein said projecting member of said end wall comprises a second cylindrical wall, said first cylindrical wall having a first outside diameter, said second cylindrical wall having a second outside diameter, said first outside diameter being larger than said second outside diameter.

32. A soil sampling device comprising:
   a body having first and second ends and a longitudinal axis, said body comprising:
      a cylindrical wall and an end wall, said cylindrical wall extending between said first and second ends of said body and about said longitudinal axis, said end wall positioned at said first end of said body, said second end of said body defining a mouth, and said mouth being adapted for inserting into soil;
   a piston positioned in said body;
   a cap releasably secured to an end portion of said cylindrical wall at said second end of said body; and
   a projecting member extending outwardly from said end wall of said body, and said end wall including an annular frangible section at a junction of said projecting member and said end wall and being adapted to break when a force is applied to said projecting member to thereby permit at least a portion of said projecting member to enter into said body and thereby push said piston along said longitudinal axis to expel a sample of soil collected in said body.

33. The soil sampling device according to claim 32, said frangible section comprises a reduced cross-section of said end wall of said body.

34. The soil sampling device according to claim 32, wherein said projecting member is integrally formed with said end wall.

35. The soil sampling device according to claim 32, wherein said piston is frictionally held in said body.

36. The soil sampling device according to claim 32, wherein said cap is frictionally held on said body.

37. The soil sampling device according to claim 36, wherein said body includes a seal, said seal frictionally holding said cap on said body.

38. The soil sampling device according to claim 37, wherein said body includes a groove for holding said seal.

39. The soil sampling device according to claim 37, wherein said cap includes a groove for receiving said seal.

40. The soil sampling device according to claim 32, wherein said body includes a pair of projecting flanges, said projecting flanges extending radially outward form said body to thereby provide a pair of pressing surfaces to ease insertion of said body into the soil.

41. The soil sampling device according to claim 40, wherein said projecting flanges are positioned at said first end of said body.

42. The soil sampling device according to claim 40, wherein said projecting flanges are generally flush with an upper surface of said end wall.

43. The soil sampling device according to claim 40, wherein at least one of said projecting flanges is reinforced by a gusset.

44. The soil sampling device according to claim 40, wherein said cap includes outwardly extending arms, said arms defining pressing surfaces for said cap to ease securement of said cap on said body.

45. The soil sampling device according to claim 44, each of said arms includes a recess for receiving a holding device for securing said cap onto said body.

46. A method of sampling a soil, the method comprising the steps of:
   providing a soil sampling device, the soil sampling device comprising:
      a body with first and second ends, the body including a cylindrical wall and an end wall, the cylindrical wall extending between the first and second ends of the body, the end wall being positioned at the first end of the body, the second end of said body defining a mouth, a piston positioned in the body, a projecting member extending outwardly from the end wall of the body, and the end wall including an annular frangible section at an interface between the projecting member and the end wall;
   inserting the mouth of the soil sampling device into soil;
   removing the soil sampling device from the soil;
   applying a force to the projecting member to thereby break the frangible section of the end wall of the soil sampling device; and
   pushing a least a portion of the projecting member into the body of the soil sampling device after breaking the frangible section to thereby expel the piston and the sample of soil collected therein from body of the soil sampling device.

47. The method of sampling a soil according the claim 46, further comprising covering the mouth of the body after removing the soil sampling device from the soil to retain the gases in the collected sample of soil.

48. The method of sampling a soil according the claim 47, wherein said step of covering includes placing a cap over the mouth of the body.

49. The method of sampling a soil according the claim 47, wherein said step of covering includes placing a cap over the mouth of the body.

50. The method of sampling a soil according to claim 47, further comprising retaining the piston in the body of the soil sampling device after the soil sample has been expelled from the body.

* * * * *